United States Patent
Teale et al.

(10) Patent No.: US 10,443,376 B2
(45) Date of Patent: Oct. 15, 2019

(54) DEVICE AND METHOD FOR CORROSION DETECTION AND FORMATION EVALUATION USING INTEGRATED COMPUTATIONAL ELEMENTS

(71) Applicant: Halliburton Energy Services, Inc., Houston, TX (US)

(72) Inventors: David Warren Teale, Spring, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/787,077

(22) PCT Filed: Jun. 20, 2013

(86) PCT No.: PCT/US2013/046894
§ 371 (c)(1),
(2) Date: Oct. 26, 2015

(87) PCT Pub. No.: WO2014/204475
PCT Pub. Date: Dec. 24, 2014

(65) Prior Publication Data
US 2016/0061028 A1   Mar. 3, 2016

(51) Int. Cl.
*E21B 47/10* (2012.01)
*E21B 49/00* (2006.01)
*G01N 17/04* (2006.01)

(52) U.S. Cl.
CPC ............. *E21B 49/00* (2013.01); *G01N 17/04* (2013.01)

(58) Field of Classification Search
CPC ....... E21B 47/102; E21B 49/00; G01N 17/04; G01N 21/31; G01N 21/88; G01N 21/954; G01N 29/265
USPC ...................... 356/614, 437, 445, 448, 241.6
See application file for complete search history.

(56) References Cited

U.S. PATENT DOCUMENTS

| | | | | |
|---|---|---|---|---|
| 5,353,637 | A * | 10/1994 | Plumb | E21B 49/008 166/101 |
| 5,517,854 | A * | 5/1996 | Plumb | E21B 49/008 73/152.59 |
| 7,413,011 | B1 | 8/2008 | Chee et al. | |
| 7,852,498 | B2 * | 12/2010 | Ohashi | G06F 3/1211 358/1.1 |
| 2003/0205083 | A1 | 11/2003 | Tubel et al. | |
| 2013/0032545 | A1 | 2/2013 | Freese et al. | |
| 2013/0081807 | A1 | 4/2013 | Dyer et al. | |
| 2013/0118733 | A1 | 5/2013 | Kumar | |
| 2014/0078499 | A1 * | 3/2014 | Tunheim | G01N 21/31 356/241.1 |
| 2015/0015884 | A1 * | 1/2015 | Russell | C09K 8/035 356/402 |

OTHER PUBLICATIONS

International Search Report and the Written Opinion of the International Searching Authority, or the Declaration, dated Mar. 27, 2014, PCT/US2013/046894, 21 pages, ISA/KR.

* cited by examiner

*Primary Examiner* — Isiaka O Akanbi
(74) *Attorney, Agent, or Firm* — Haynes and Boone, LLP

(57) ABSTRACT

An optical computing device and method for (1) determining and/or monitoring corrosion data in a given environment and (2) evaluating a downhole formation, both being accomplished in real-time by deriving the data from the output of an optical element.

35 Claims, 5 Drawing Sheets

US 10,443,376 B2

DEVICE AND METHOD FOR CORROSION DETECTION AND FORMATION EVALUATION USING INTEGRATED COMPUTATIONAL ELEMENTS

The present application is a U.S. National Stage patent application of International Patent Application No. PCT/US2013/046894, filed on Jun. 20, 2013, the benefit of which is claimed and the disclosure of which is incorporated herein by reference in its entirety.

FIELD OF THE INVENTION

The present invention relates generally to optical sensors and, more specifically, to an Integrated Computational Element ("ICE") based optical device for real-time corrosion detection/monitoring in a variety of environments, as well as downhole formation evaluation.

BACKGROUND

Corrosion is measured in many industries for a variety of reasons. One such industry is hydrocarbon exploration and recovery. Downhole corrosion measurement requires a broad range of data to characterize the presence of corrosion by-products, material loss, or life expectancy. Traditionally, this data could only be obtained through extensive laboratory study or time-consuming sample testing in the field.

However, these conventional corrosion measurement techniques are disadvantageous. Laboratory methods are labor intensive, do not provide a direct correlation to actual corrosion, and are time-consuming since the analysis is performed post-extraction. Testing in the field is limited by the lack of sufficient space to position samples (accessibility) and also may be limited to non-destructive methods. Down-hole environments and typical wellbore architectures do not provide easy access for sample placement. Moreover, costs associated with daily operations and wellbore intervention operations are cost prohibitive.

In hydrocarbon exploration and recovery, it is also necessary to perform formation evaluation in order to determine when the payzone has been penetrated. A number of techniques currently exist which include (1) nuclear detection tools and sensors, (2) resistivity tools, (3) hydrophone/accelerometer based acoustic/seismic technology, and (4) core drilling techniques which require secondary evaluation. However, such conventional methods are disadvantageous in that additional tools and equipment are needed in the space-restricted downhole environment, and can require hazardous or radioactive materials.

Accordingly, there is a need in the art for a cost-effective, compact and power efficient system in which to (1) detect/monitor corrosion data in a given environment and (2) to perform formation evaluation, both being performed in real-time.

DESCRIPTION OF ILLUSTRATIVE EMBODIMENTS

Figure 1:
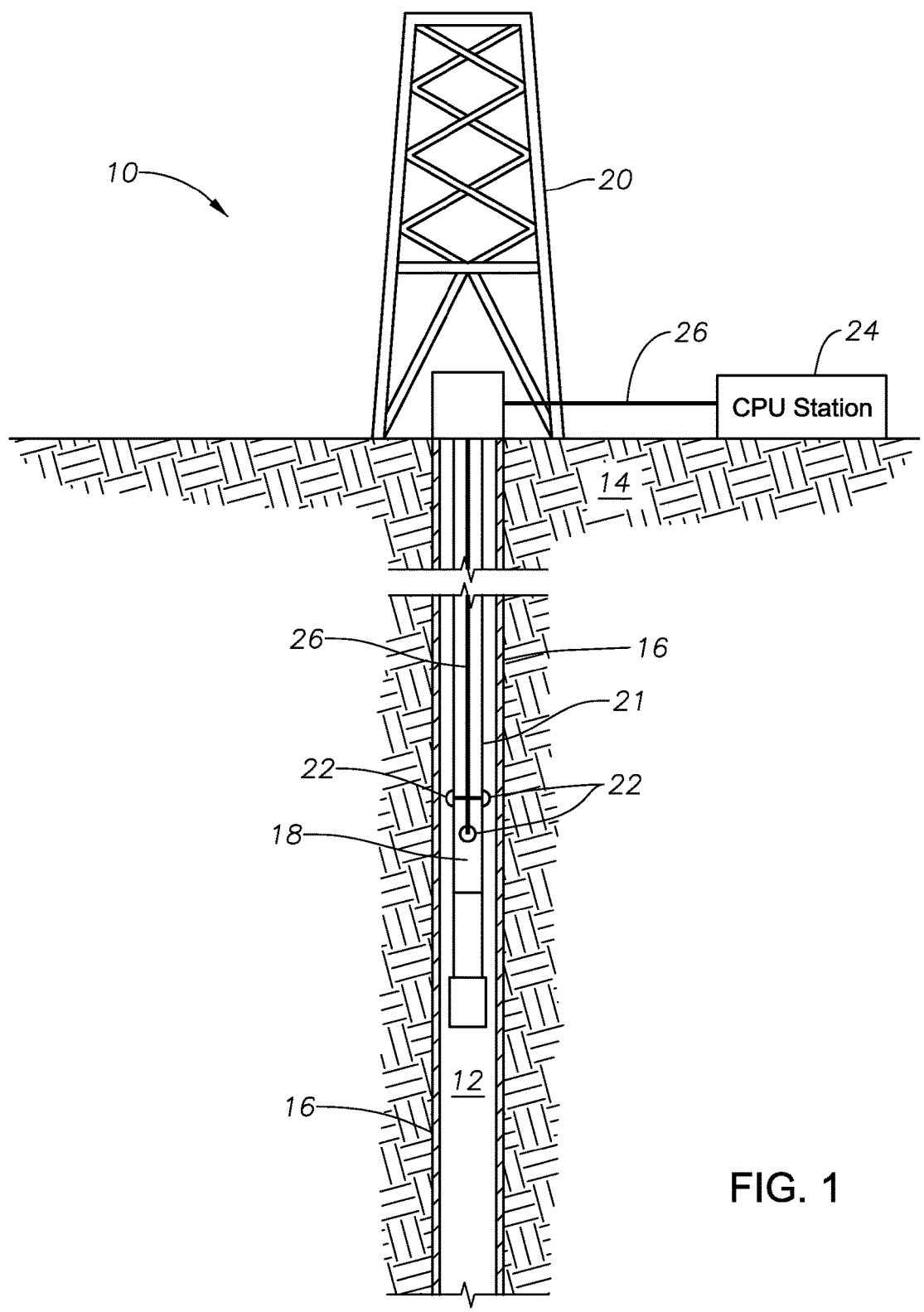
FIG. 1 illustrates a well system having optical computing devices deployed therein for corrosion detection and/or formation evaluation according to certain exemplary embodiments of the present invention.

Illustrative embodiments and related methodologies of the present invention are described below as they might be employed in an optical computing device and method to determine the rate of corrosion of a sample in a variety of environments, and to evaluation various formations along a wellbore. In the interest of clarity, not all features of an actual implementation or methodology are described in this specification. Also, the "exemplary" embodiments described herein refer to examples of the present invention. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

Certain exemplary embodiments of the present invention are directed to an optical computing device that determines and monitors corrosion and decomposition of materials data in real-time by deriving the data directly from the output of an optical element (ICE, for example). In certain embodiments, the optical computing device is a dedicated, single-purpose device that obtains corrosion data, while in other embodiments the optical computing device acts as a dual-purpose device that obtains corrosion data and various other characteristic data of the measured sample. In either embodiment, the present invention determines the corrosion of a sample based on the physical and/or optical responses of the sample over time. In the dual purpose embodiment, the corrosion data is derived as a secondary function of the optical computing device and does not interfere with its primary mode of operation (i.e., detecting characteristic data). Accordingly, the present invention provides real-time corrosion monitoring in a variety of space-limited or power constrained environments.

As further described herein, exemplary embodiments of the computing devices can derive and record material condition and environmental responses over time by way of spectral data. This allows for active monitoring of various environments, such as, for example, wellbore structures, downhole tools, or targeted control samples. Active monitoring may predict damage, estimate life expectancy or provide support for a robust risk management program. As will be understood by those ordinarily skilled in the art having the benefit of this disclosure, suitable placement of the optical computing devices would enable corrosion monitoring at various locations throughout the desired environment (completion string, for example).

In addition to corrosion detection, certain other exemplary embodiments of the present invention are directed to optical computing devices and methods to evaluate and record formation data downhole in real-time by deriving the data directly from the output of an optical element. Such formation data evaluation may include, for example, determination of the presence of formation chemical composition, sand fraction/detection, porosity, water cut, and identifying geological or man-made tracers or tags which indicate the presence of a defined formation. As described herein, the optical devices would be positioned proximal to the formation or sample target. In certain embodiments, the formation data is obtained in real-time directly from the optical output of the optical element, while in other embodiments the formation evaluation is conducted remotely (at surface, for example) using data transmitted from the optical computing device.

In the most preferred embodiment, the optical computing devices described herein utilize one or more ICEs (also known as a Multivariate Optical Element ("MOE")) as the optical elements. Alternatively, however, narrow band filters may also be utilized as the optical elements. Nevertheless, as will be understood by those ordinarily skilled in the art having the benefit of this disclosure, an ICE is an optical element configured to receive an input of electromagnetic radiation from a substance or sample of the substance and produce an output of electromagnetic radiation that corresponds to a characteristic of the sample. Fundamentally, optical computing devices utilize the ICE to perform calculations, as opposed to the hardwired circuits of conventional electronic processors. When electromagnetic radiation interacts with a substance, unique physical and chemical information about the substance is encoded in the electromagnetic radiation that is reflected from, transmitted through, or radiated from the sample. Thus, the optical computing device, through use of the ICE, is capable of extracting the information of one or multiple characteristics/properties or analytes within a sample, and converting that information into a detectable output regarding the overall properties of a sample.

Further discussion of the design and operation of ICEs and optical computing devices can be found in, for example, U.S. Pat. No. 6,198,531, entitled "OPTICAL COMPUTATIONAL SYSTEM," issued to Myrick et al. on Mar. 6, 2001; U.S. Pat. No. 7,697,141, entitled "IN SITU OPTICAL COMPUTATION FLUID ANALYSIS SYSTEM AND METHOD," issued to Jones et al. on Apr. 13, 2010; and U.S. Pat. No. 8,049,881, entitled "OPTICAL ANALYSIS SYSTEM AND METHODS FOR OPERATING MULTIVARIATE OPTICAL ELEMENTS IN A NORMAL INCIDENCE ORIENTATION," issued to Myrick et al. on Nov. 1, 2011, each being owned by the Assignee of the present invention, Halliburton Energy Services, Inc., of Houston, Tex., the disclosure of each being hereby incorporated by reference in its entirety.

As further described herein, the exemplary optical computing devices determine corrosion or perform formation evaluation through utilization of the unique physical and chemical information encoded in the radiation, or light spectra, emanating from the sample. As will be understood by those ordinarily skilled in the art having the benefit of this disclosure, the sample behaves according to laws of physics whereby the sample material undergoes various physical changes due to external effects (corrosion, for example). It is this principle which allows the present inventive optical computing device to measure the corresponding effect (corrosion). In other words, the present invention collects spectral information as a function of physical variables of the sample. Thus, as the physical variables are altered due to corrosive changes, there is a corresponding shift in the spectral information relative to the baseline data. Such physical variations may manifest themselves as elemental corrosion by-products, material loss, or generation of physical defects such as, for example, pitting of the sample material. Therefore, the present invention analyzes the baseline shift in the spectral information to determine the corresponding corrosion.

Additionally, the physical variations of the sample can also provide data that indicates the presence of a formation, such as, for example, data indicating formation chemistry, sand fraction, porosity, watercut, or natural or man-made tracers or tags. Formation evaluation parameters may be tailored as desired and utilized by the optical computing devices to determine when the desired formation has been reached in real-time. Parameters may include, for example, formation porosity, identification of known rock formations, or the presence of products, including gas and/or petroleum based products. Such parameters may be identified and mapped so that the target zone is located and the equipment is optimized for recovery.

In certain exemplary embodiments which measure corrosion, a historical record of the material signature over time can be generated to analyze rates of decay. Such data may be collected from a variety of samples, such as, for example, downhole tools, wellbore structural components or specific material specimens strategically placed in the wellbore and exposed to the environment. Through comparison of this sample spectral data to a reference material standard (i.e., baseline data), the present invention may determine rates of corrosion, material loss, etc. Such baseline data may be attained from empirical data (lab data, for example) or may be historical measurements taken of the sample by the optical computing device itself. In other embodiments, the derived data can also supply information to predict life expectancy of the sample or to determine whether remedial action (chemical treatment or intervention in the given environment, for example) is necessary.

The optical computing devices described herein may be utilized in a variety of environments. Such environments may include, for example, downhole well or completion applications. Other environments may include those as diverse as those associated with surface and undersea monitoring, satellite or drone surveillance, pipeline monitoring, or even sensors transiting a body cavity such as a digestive tract. Within those environments, the optical computing devices are utilized to detect/monitor corrosion and evaluate formations, in addition to detecting various compounds or characteristics in order to monitor, in real time, various phenomena occurring within the environment.

Although the optical computing devices described herein may be utilized in a variety of environments, the following description will focus on downhole well applications. FIG. 1 illustrates a plurality of optical computing devices 22 positioned along a workstring 21 extending along a downhole well system 10 according to certain exemplary embodiments of the present invention. Workstring 21 may be, for example, a logging assembly, production string or drilling assembly. Well system 10 comprises a vertical wellbore 12 extending down into a hydrocarbon formation 14 (although not illustrated, wellbore 12 may also comprise one or more lateral sections). Wellbore equipment 20 is positioned atop vertical wellbore 12, as understood in the art. Wellbore equipment may be, for example, a blow out preventer, derrick, floating platform, etc. As understood in the art, after vertical wellbore 12 is formed, tubulars 16 (casing, for example) are extended therein to complete wellbore 12.

One or more optical computing devices 22 may be positioned along wellbore 12 at any desired location. In certain embodiments, optical computing devices 22 are positioned along the internal or external surfaces of downhole tool 18 (as shown in FIG. 1) which may be, for example, intervention equipment, surveying equipment, or completion equipment including valves, packers, screens, mandrels, gauge mandrels, in addition to casing or tubing tubulars/joints as referenced below. Alternatively, however, optical computing devices 22 may be permanently or removably attached to tubulars 16 and distributed throughout wellbore 12 in any area in which corrosion detection/monitoring or formation evaluation is desired. Optical computing devices 22 may be coupled to a remote power supply (located on the surface or a power generator positioned downhole along the wellbore, for example), while in other embodiments each optical computing device 22 comprises an on-board battery. Moreover, optical computing devices 22 are communicably coupled to a CPU station 24 via a communications link 26, such as, for example, a wireline, inductive coupling or other suitable communications link. Those ordinarily skilled in the art having the benefit of this disclosure will readily appreciate that the number and location of optical computing devices 22 may be manipulated as desired.

Each optical computing device 22 comprises an ICE that optically interacts with a sample of interest (wellbore fluid, downhole tool component, tubular, formation, for example) to determine the corrosion of the sample or the presence of a defined formation. In certain exemplary embodiments, optical computing devices 22 may be dedicated to corrosion detection or formation evaluation, or alternatively, they may serve the multi-purpose of sample corrosion and characteristic detection, as well as formation evaluation. For corrosion detection, exemplary characteristics determined by optical computing devices 22 include the presence and quantity of corrosive elemental by-products, sample material loss, or generation of physical defects in the sample material. Exemplary corrosive by-products may be, for example, acids, oxides, molds or bacteria which begin to accumulate on the sample base material over time. In addition, optical computing devices 22 may also determine the presence and quantity of specific inorganic gases such as, for example, $CO_2$ and $H_2S$, organic gases such as methane (C1), ethane (C2) and propane (C3) and saline water, in addition to dissolved ions (Ba, Cl, Na, Fe, or Sr, for example) or various other characteristics (p.H., density and specific gravity, viscosity, total dissolved solids, sand content, etc.). Furthermore, the presence of formation characteristic data (porosity, formation chemical composition, etc.) may also be determined. In certain embodiments, a single optical computing device 22 may detect a single characteristic, while in others a single optical computing device 22 may determine multiple characteristics, as will be understood by those ordinarily skilled in the art having the benefit of this disclosure.

CPU station 24 comprises a signal processor (not shown), communications module (not shown) and other circuitry necessary to achieve the objectives of the present invention, as will be understood by those ordinarily skilled in the art having the benefit of this disclosure. In addition, it will also be recognized that the software instructions necessary to carry out the objectives of the present invention may be stored within storage located in CPU station 24 or loaded into that storage from a CD-ROM or other appropriate storage media via wired or wireless methods. Communications link 26 provides a medium of communication between CPU station 24 and optical computing devices 22. Communications link 26 may be a wired link, such as, for example, a wireline or fiber optic cable extending down into vertical wellbore 12. Alternatively, however, communications link 26 may be a wireless link, such as, for example, an electromagnetic device of suitable frequency, or other methods including acoustic communication and like devices.

In certain exemplary embodiments, CPU station 24, via its signal processor, controls operation of each optical computing device 22. In addition to sensing operations, CPU station 24 may also control activation and deactivation of optical computing devices 22. Optical computing devices 22 each include a transmitter and receiver (transceiver, for example) (not shown) that allows bi-directional communication over communications link 26 in real-time. In certain exemplary embodiments, optical computing devices 22 will transmit all or a portion of the corrosion/formation or other sample characteristic data to CPU station 24 for further analysis. However, in other embodiments, such analysis is completely handled by each optical computing device 22 and the resulting data is then transmitted to CPU station 24 for storage or subsequent analysis. In either embodiment, the processor handling the computations analyzes the characteristic data and, through utilization of Equation of State ("EOS") or other optical analysis techniques, derives the corrosion, formation and/or other characteristic indicated by the transmitted data, as will be readily understood by those ordinarily skilled in the art having the benefit of this disclosure.

Still referring to the exemplary embodiment of FIG. 1, optical computing devices 22 are positioned along workstring 21 at any desired location. In this example, optical computing devices 22 are positioned along the outer diameter of downhole tool 18. Optical computing devices 22 have a temperature and pressure resistant housing sufficient to withstand the harsh downhole environment. A variety of materials may be utilized for the housing, including, for example, stainless steels and their alloys, titanium and other high strength metals, and even carbon fiber composites and sapphire or diamond structures, as understood in the art. In certain embodiments, optical computing devices 22 are dome-shaped modules (akin to a vehicle dome light) which may be permanently or removably attached to a surface using a suitable method (welding, magnets, etc.). Module housing shapes may vary widely, provided they isolate components from the harsh down-hole environment while still allowing a unidirectional or bidirectional optical (or electromagnetic radiation) pathway from sensor to the sample of interest. As will be understood by those ordinarily skilled in the art having the benefit of this disclosure, dimensions would be determined by the specific application and environmental conditions.

Alternatively, optical computing devices 22 may form part of downhole tool 18 (as shown in FIG. 1) along its inner diameter (to detect the presence of corrosive by-products in fluids flowing through tool 18 or corrosion along the inner surface of tool 18, for example) or outer diameter (to detect corrosion along the tubulars 16 or the presence of corrosive by-products in fluids flowing through the annulus between workstring 21 and tubulars 16 or formation characteristic data, for example). In other embodiments as will be described below, optical computing devices 22 may be coupled to downhole tool 18 using an extendable arm (adjustable stabilizer, casing scraper, downhole tractor, for example) in order to extend optical computing device 22 into close proximity with another surface (casing, tool body, formation, etc.) to thereby detect corrosion or to perform formation evaluation. As previously described, optical computing devices 22 may also be permanently affixed to the inner diameter of tubular 16 by a welding or other suitable process. However, in yet another embodiment, optical computing devices 22 are removably affixed to the inner diameter of tubulars 16 using magnets or physical structures so that optical computing devices 22 may be periodically removed for service purposes or otherwise. In such embodiments, corrosion along various parts of the workstring may be continually monitored and/or formation evaluation may be continually performed via analysis of cuttings or other elements passing by the computing devices.

As mentioned above, those ordinarily skilled in the art having the benefit of this disclosure realize the optical computing devices described herein may be housed or packaged in a variety of ways. In addition to those described herein, exemplary housings also include those described in Patent Cooperation Treaty Application No. PCT/US2013/046840, filed on Jun. 20, 2013, entitled "IMPLEMENTATION CONCEPTS AND RELATED METHODS FOR OPTICAL COMPUTING DEVICES, the disclosure of which is hereby incorporated by reference in its entirety.

Figure 2:
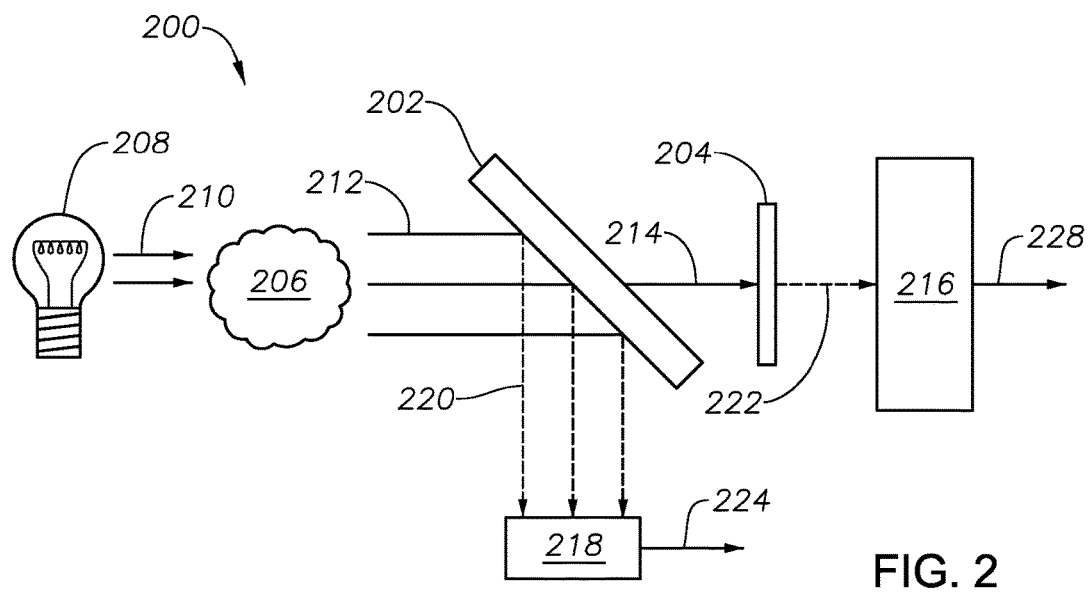
FIG. 2 is a block diagram of an optical computing device employing a transmission mode design for corrosion detection and/or formation evaluation, according to certain exemplary embodiments of the present invention.

FIG. 2 is a block diagram of an optical computing device 200 employing a transmission mode design, according to certain exemplary embodiments of the present invention. An electromagnetic radiation source 208 may be configured to emit or otherwise generate electromagnetic radiation 210. As understood in the art, electromagnetic radiation source 208 may be any device capable of emitting or generating electromagnetic radiation. For example, electromagnetic radiation source 208 may be a light bulb, light emitting device, laser, blackbody, photonic crystal, or X-Ray source, etc. In one embodiment, electromagnetic radiation 210 may be configured to optically interact with the sample 206 (wellbore fluid flowing through wellbore 12 or a portion of the formation 14, for example) and generate sample-interacted light 212 directed to a beam splitter 202. Sample 206 may be any fluid (liquid or gas), solid substance or material such as, for example, downhole tool components, tubulars, rock formations, slurries, sands, muds, drill cuttings, concrete, other solid surfaces, etc. In other embodiments, however, sample 206 is a multiphase wellbore fluid (comprising oil, gas, water, solids, for example) consisting of a variety of fluid characteristics such as, for example, elemental corrosive by-products, elements generated by sample material loss, C1-C4 and higher hydrocarbons, groupings of such elements, and saline water. However, if the sample where a downhole tool component, the characteristic data may correspond to physical defects in the surface of the component such as, for example, pitting.

Sample 206 may be provided to optical computing device 200 through a flow pipe or sample cell, for example, containing sample 206, whereby it is introduced to electromagnetic radiation 210. Alternatively, optical computing device 200 may utilize an optical configuration consisting of an internal reflectance element which analyzes the wellbore fluid as it flows thereby or which analyzes the surface of the sample (formation surface, for example). While FIG. 2 shows electromagnetic radiation 210 as passing through or incident upon the sample 206 to produce sample-interacted light 212 (i.e., transmission or fluorescent mode), it is also contemplated herein to reflect electromagnetic radiation 210 off of the sample 206 (i.e., reflectance mode), such as in the case of a sample 206 that is translucent, opaque, or solid, and equally generate the sample-interacted light 212.

After being illuminated with electromagnetic radiation 210, sample 206 containing an analyte of interest (a characteristic of the sample, for example) produces an output of electromagnetic radiation (sample-interacted light 212, for example). As previously described, sample-interacted light 212 also contains spectral information that reflects physical variations of the sample used to determine corrosion in the environment or sample surface, as well as to determine the presence of a defined formation. Ultimately, CPU station 24 (or a processor on-board device 200) analyzes this spectral information in conjunction with baseline spectral information to evaluate the presence of a formation and/or to derive a corrosive rate or decay, material loss, etc. Although not specifically shown, one or more spectral elements may be employed in optical computing device 200 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Still referring to the exemplary embodiment of FIG. 2, beam splitter 202 is employed to split sample-interacted light 212 into a transmitted electromagnetic radiation 214 and a reflected electromagnetic radiation 220. Transmitted electromagnetic radiation 214 is then directed to one or more optical elements 204. Optical element 204 may be a variety of optical elements such as, for example, one or more narrow band optical filters or ICEs arranged or otherwise used in series in order to determine the characteristics of sample 206. In those embodiments using ICEs, the ICE may be configured to be associated with a particular characteristic of sample 206 or may be designed to approximate or mimic the regression vector of the characteristic in a desired manner, as would be understood by those ordinarily skilled in the art having the benefit of this disclosure. Additionally, in an alternative embodiment, optical element 204 may function as both a beam splitter and computational processor, as will be understood by those same ordinarily skilled persons.

Nevertheless, transmitted electromagnetic radiation 214 then optically interacts with optical element 204 to produce optically interacted light 222. In this embodiment, optically interacted light 222, which is related to the characteristic or analyte of interest, is conveyed to detector 216 for analysis and quantification. In addition to the characteristic or analyte of interest, optically interacted light 22 also contains spectral data utilized to derive corrosion or to determine the presence of a defined formation. Detector 216 may be any device capable of detecting electromagnetic radiation, and may be generally characterized as an optical transducer. For example, detector 216 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, and/or combinations thereof, or the like, or other detectors known to those ordinarily skilled in the art. Detector 216 is further configured to produce an output signal 228 in the form of a voltage that corresponds to the particular corrosive element or decay, formation characteristic, or other characteristic of the sample 206. In at least one embodiment, output signal 228 produced by detector 216 and the corrosive element/formation characteristic concentration of the sample 206 may be directly proportional. In other embodiments, the relationship may be a polynomial function, an exponential function, and/or a logarithmic function.

Optical computing device 200 includes a second detector 218 arranged to receive and detect reflected electromagnetic radiation and output a normalizing signal 224. As understood in the art, reflected electromagnetic radiation 220 may include a variety of radiating deviations stemming from electromagnetic radiation source 208 such as, for example, intensity fluctuations in the electromagnetic radiation, interferent fluctuations (for example, dust or other interferents passing in front of the electromagnetic radiation source), combinations thereof, or the like. Thus, second detector 218 detects such radiating deviations as well. In an alternative embodiment, second detector 218 may be arranged to receive a portion of the sample-interacted light 212 instead of reflected electromagnetic radiation 220, and thereby compensate for electromagnetic radiating deviations stemming from the electromagnetic radiation source 208. In yet other embodiments, second detector 218 may be arranged to receive a portion of electromagnetic radiation 210 instead of reflected electromagnetic radiation 220, and thereby likewise compensate for electromagnetic radiating deviations stemming from the electromagnetic radiation source 208. Those ordinarily skilled in the art having the benefit of this disclosure will realize there are a variety of design alterations which may be utilized in conjunction with the present invention.

Although not shown in FIG. 2, in certain exemplary embodiments, detector 216 and second detector 218 may be communicably coupled to a signal processor (not shown) on-board optical computing device 200 such that normalizing signal 224 indicative of electromagnetic radiating deviations may be provided or otherwise conveyed thereto. The signal processor may then be configured to computationally combine normalizing signal 224 with output signal 228 to provide a more accurate determination of the corrosion and/or characteristic of sample 206. However, in other embodiments that utilized only one detector, the signal processor would be coupled to the one detector. Nevertheless, in the embodiment of FIG. 2, for example, the signal processor computationally combines normalizing signal 224 with output signal 228 via principal component analysis techniques such as, for example, standard partial least squares which are available in most statistical analysis software packages (for example, XL Stat for MICROSOFT® EXCEL®; the UNSCRAMBLER® from CAMO Software and MATLAB® from MATHWORKS®), as will be understood by those ordinarily skilled in the art having the benefit of this disclosure. Thereafter, the resulting data is then transmitted to CPU station 24 via communications link 26 for further operations.

As described herein, the formation may be evaluated or corrosion determined by a processor on-board optical computing devices 22 or by a processor in CPU station 24. In either embodiment, there are a variety of ways in which to determine the corrosion. In one example, output signal 228 comprises spectral data indicative of various physical or chemical characteristics of the sample. Such characteristic data may be, for example, corrosive elemental by-products (acids, oxides, etc.), elemental particles (metals, minerals, etc.) generated due to sample material loss, or physical defects in the sample material itself. As the sample corrodes, the corresponding light spectrum shifts from the pure material of the sample through various corrosive stages of the sample material. Since it is understood that spectral data is contingent upon physical or chemical characteristics of the sample, the processor handling the computations will compare the received spectral data with baseline spectral data. In certain embodiments, the baseline data is received from empirical data. The empirical data may have been acquired, for example, through lab experimentation in which the sample material was purposely corroded from a pure material (i.e., baseline data) through any desired material loss. Baseline data can also be acquired through core drilling/sampling and brought to surface for identification and cataloging. Alternatively, the baseline data may be derived from corrosive measurements of the sample taken by the computing device itself at a point earlier in time.

Based upon this comparison of spectral and baseline data, the processor maps the computed spectral change to a scale to derive the corresponding corrosion. This may be accomplished in a variety of ways, such as, for example, classical least squares fitting of the dependent response (i.e., normalized tracer concentration) with the independent variable (i.e., corrosion), which is an example of univariate calibration. Other modeling techniques may include multivariate statistics, Partial least squares, Principal component regression, and multiple curve resolution. Alternatively, a variety of other analytical tools may be utilized by the processor to determine the rate of decay of the sample. In addition, the processor evaluates the presence of a defined formation by comparing the measured spectral information to known patterns established for the desired target formation. In one example, optical filters may be predefined to optically isolate for the desired target formation.

Figure 3:
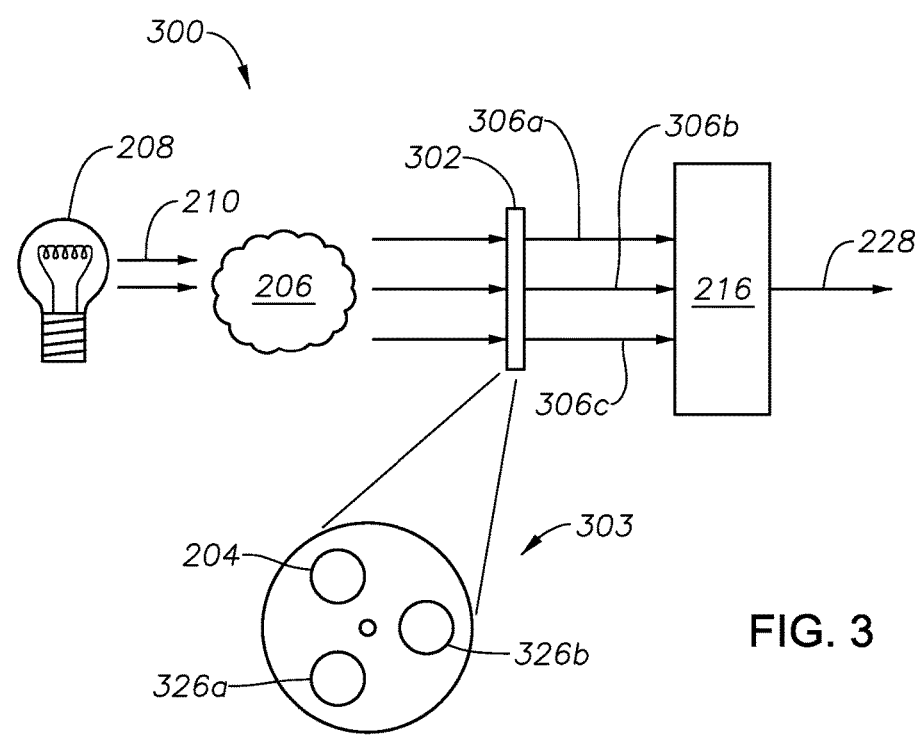
FIG. 3 is a block diagram of another optical computing device employing a time domain mode design for corrosion detection and/or formation evaluation, according to certain exemplary embodiments of the present invention.

FIG. 3 illustrates a block diagram of yet another optical computing device 300 employing a time domain mode design, according to certain exemplary embodiments of the present invention. Optical computing device 300 is somewhat similar to optical computing device 200 described with reference to FIG. 2 and, therefore, may be best understood with reference thereto, where like numerals indicate like elements. Optical computing device 300 may include a movable assembly 302 having at least one optical element 204 and two additional optical elements 326a and 326b associated therewith. As illustrated, the movable assembly 302 may be characterized at least in one embodiment as a rotating disc 303, such as, for example, a chopper wheel, wherein optical elements 204, 326a and 326b are radially disposed for rotation therewith. FIG. 3 also illustrates corresponding frontal views of the moveable assembly 302, which is described in more detail below.

Those ordinarily skilled in the art having the benefit of this disclosure will readily recognize, however, that movable assembly 302 may be characterized as any type of movable assembly configured to sequentially align at least one detector with optically interacted light and/or one or more optical elements. Each optical element 204, 326a and 326b may be similar in construction to those as previously described herein, and configured to be either associated or disassociated with a particular corrosive, formation or other characteristic of the sample 206. Although three optical elements are described, more or less optical elements may be employed along movable assembly 302 as desired.

In certain exemplary embodiments, rotating disc 303 may be rotated at a frequency of about 0.1 RPM to about 30,000 RPM. In operation, rotating disc 303 may rotate such that the individual optical elements 204, 326a and 326b may each be exposed to or otherwise optically interact with the sample-interacted light 212 for a distinct brief period of time. Upon optically interacting with the sample-interacted light 212, optical element 204 is configured to generate optically interacted light 306a (a first beam, for example), optical element 326a is configured to generate a second optically interacted light 306b (a second beam, for example) and optical element 326b is configured to generate a normalized electromagnetic radiation 306c (a normalization beam, for example). Detector 216 then receives each beam 306a-c and thereby generates a first, second and third output signal, respectively (output signal 228 comprises the first, second and third signals). Accordingly, a signal processor (not shown) communicatively coupled to detector 216 utilizes the output signal to computationally determine the sample characteristics.

Moreover, in certain exemplary embodiments, detector 216 may be configured to time multiplex beams 306a-c between the individually-detected beams. For example, optical element 204 may be configured to direct first beam 306a toward the detector 216 at a first time T1, optical element 326a may be configured to direct second beam 306b toward the detector 216 at a second time T2, and optical element 326b may be configured to direct third beam 306c toward detector 216 at a third time T3. Consequently, detector 216 receives at least three distinct beams of optically-interacted light which may be computationally combined by a signal processor (not shown) coupled to detector 216 in order to provide an output in the form of a voltage that corresponds to the corrosive, formation and/or other characteristic of the sample, as previously described. In certain alternate embodiments, beams 306a-c may be averaged over an appropriate time domain (for example, about 1 millisecond to about 1 hour) to more accurately determine the corrosion and/or characteristic of sample 206. As previously described, detector 216 is positioned to detect first, second and third beams 306a-c in order to produce output signal 228. In this embodiment, a signal processor (not shown) may be communicably coupled to detector 216 such that output signal 228 may be processed as desired to computationally determine the corrosive, formation and/or other characteristic of sample 206.

Those ordinarily skilled in the art having the benefit of this disclosure realize the aforementioned optical computing devices are exemplary in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). In addition, the optical computing devices may comprise a parallel processing configuration whereby the sample-interacted light is split into multiple beams. The multiple beams may then simultaneously go through corresponding ICEs, whereby multiple corrosive characteristics and/or analytes of interest are simultaneously detected. The parallel processing configuration is particularly useful in those applications that require extremely low power or no moving parts. In yet another alternate embodiment, various single or multiple ICEs may be positioned in series in a single optical computing device. This embodiment is particularly useful if it is necessary to measure the corrosive, formation or other concentrations of the analytes in different locations (in each individual mixing pipe, for example). It is also sometimes helpful if each of the ICEs use two substantially different light sources (UV and IR, for example) to cover the optical activity of all the corrosive characteristics or analytes of interest (i.e., some analytes might be only UV active, while others are IR active). Nevertheless, those ordinarily skilled in the art having the benefit of this disclosure will realize the choice of a specific optical configuration is mainly dependent upon the specific application and analytes of interest.

Figure 4:
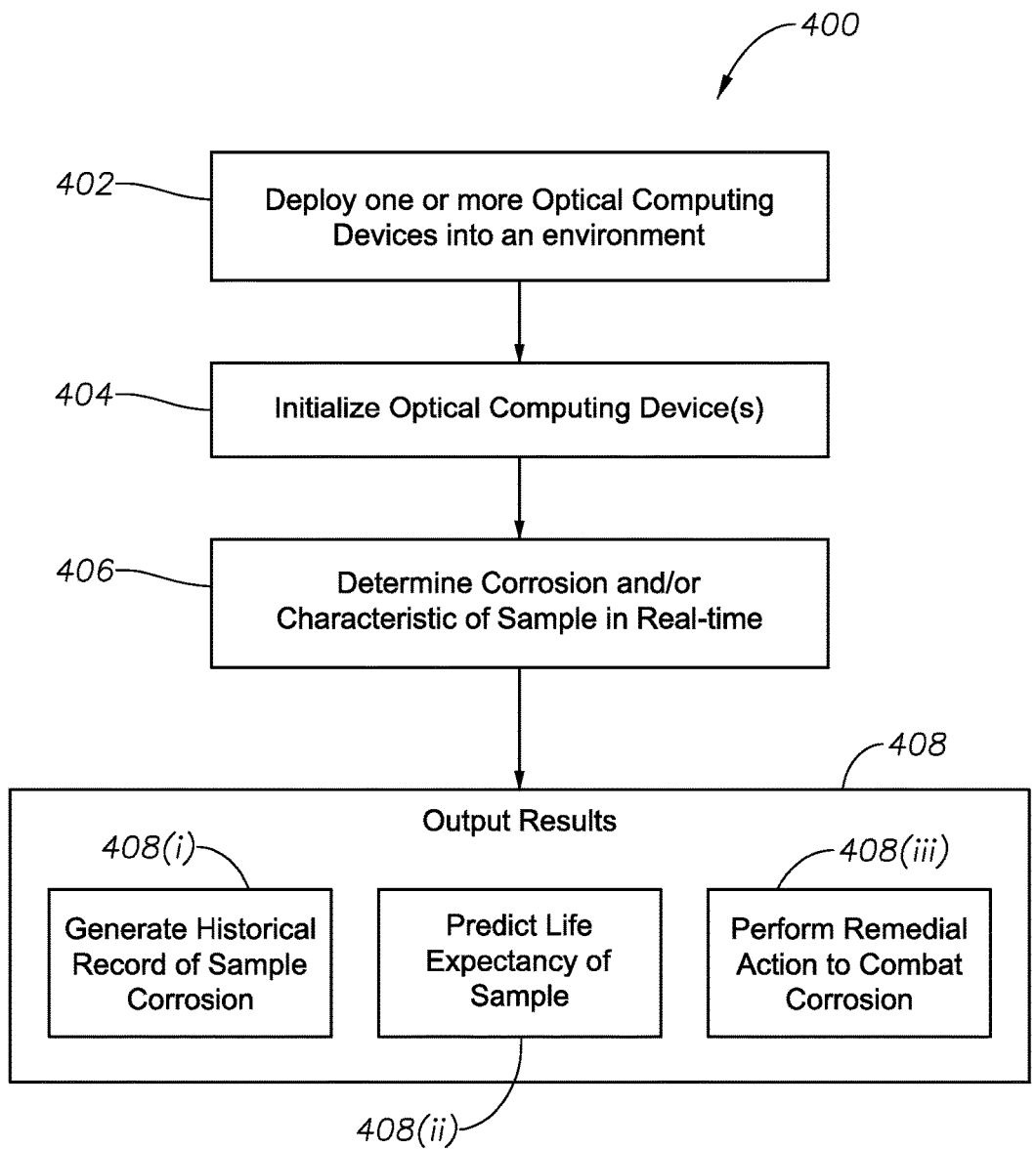
FIG. 4 is a flow chart of a corrosion detection methodology performed by an optical computing device in accordance to certain exemplary methods of the present invention.

In view of the foregoing description, an exemplary methodology of the present invention will now be described with reference to the flow chart 400 of FIG. 4. As stated throughout this description, the optical computing devices described herein may be utilized to detect corrosion in a variety of environments. In one such application at block 402, one or more optical computing devices are deployed in an environment (downhole well, for example) as part of a monitoring system. When it is desired to perform corrosion detection, CPU station 24 initializes one or more optical computing devices at block 404. As wellbore fluid, tool components, or other samples of interest flow through the well past the activated optical computing devices (or the computing devices are positioned adjacent to the samples), the optical elements contained therein optically interact with the radiation emanating from the sample to determine the presence of corrosive elements or other characteristics of the sample at block 406. Alternatively, at block 406, the optical computing device (or the CPU station) may also utilize the radiation emanating from the sample to determine one or more other characteristics of the sample (presence of C1-C4 hydrocarbon, for example). The determination of block 406 may be performed in real-time by the optical computing device itself or corrosive/characteristic data is generated by the computing device and transmitted to the CPU station for further processing in real-time.

As previously described, to determine corrosion at block 406, the processor compares the signal received from the optical computing device to baseline data of the sample. In one methodology, the baseline data is empirical data. Alternatively, the baseline data may be a sample measurement taken by the optical computing device at time T1, and then compared to a second sample measurement taken by the optical computing device at time T2. In such an embodiment, empirical data would not be necessary since the sample itself will provide the baseline data.

At block 408, the processor on board the computing device or remote CPU station outputs the results. Such results may be output in a variety of ways, such as, for example, via a graphical user interface, 2D or 3D earth models, etc., as understood in the art. In addition, the processor may generate a historical record of the rate of corrosion of the sample over time at block 408(i). In other embodiments, the processor may predict life expectancy of the sample based upon the corrosive measurement signal received from the computing device at block 408(ii). Here, for example, life expectancy can be predicted by tracking the amount of material loss or the rate of material loss. For load bearing mechanical structures, as material is lost, the cross section changes. Material strength under load would be compromised depending on the level and depth of the corrosion.

Material loss limits can be set if the environment and materials have known loads/stresses and known corrosion or loss behaviors. When limits are reached, recommendations can be made for replacement, change in load condition, or treatment. Corrosion products can also be compared to known laboratory sample lifetimes given a certain set of input environmental factors (chemistry, pH, temperature, etc.). In other words, the ICE predicts an instantaneous level of corrosion based on the presence of the tracer, which will vary over time. The processor integrates the corrosion to produce a rate. The rate/total corrosion (based on the total amount of tracer available) would yield the time to reach the endpoint (i.e., life expectancy). This comparison can establish chemicals present and known corrosion mechanisms so that proper treatment chemicals can be injected to prevent further damage or, if the corrosion cannot be treated, life expectancy can be predicted based on known correlations. One example would be inter-granular corrosion. In other embodiments, lab samples tested with similar compounds could be utilized to establish corrosion limits and estimate useful life/load capacity. At block 408(*iii*), the processor may also determine whether remedial action is necessary to combat the detected corrosion. For example, mud having anti-corrosive chemicals may be automatically pumped downhole.

In certain other exemplary embodiments, corrosive data from the optical computing device can be utilized locally in the well at the device or transmitted to the surface or other remote data processing equipment inside or outside the well to trigger alert signals based on predetermined criteria, such as, for example, corrosive element concentration limits. Crossing these boundary limits may trigger alerts and remedial actions to correct further corrosion, process deficiencies, or conditions. Examples include, but are not limited to, the following: operator alerts at surface, automated valve actuation at surface or down hole to alter flow conditions, trigger/control of additional injection fluids (such as mud to combat corrosion) and chemicals for treatments and control of scale and other unwanted conditions.

Figure 5:
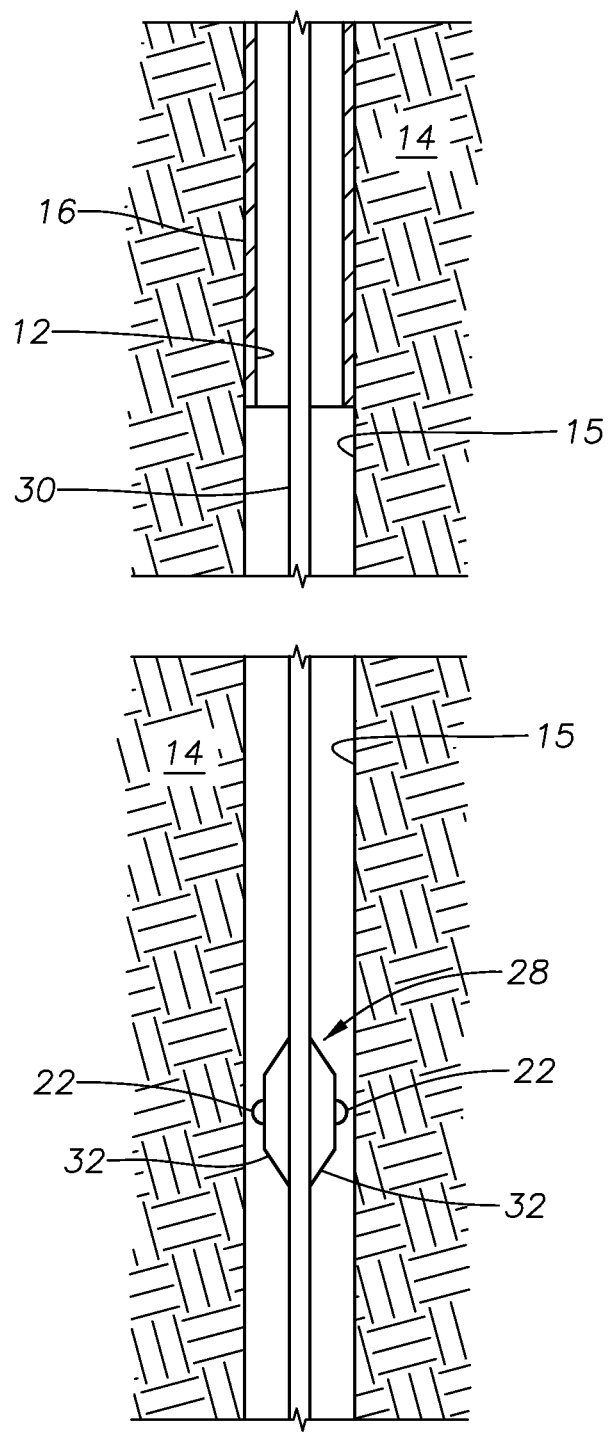
FIG. 5 illustrates the well system of FIG. 1 in which optical computing devices has been deployed via coil tubing for formation evaluation, according to certain exemplary embodiments of the present invention.

FIG. 5 illustrates the well system of FIG. 1 in which optical computing devices has been deployed via coil tubing for formation evaluation, according to certain exemplary embodiments of the present invention. Unlike in FIG. 1, here optical computing devices 22 have been deployed down wellbore 12 into open hole 15 using coiled tubing 30. As will be understood by those ordinarily skilled in the art having the benefit of this disclosure, accuracy of the formation measurement is based on signal to noise ratio and the amount of signal loss at the detector. Therefore, deployment of optical computing devices 22 must be close enough to the formation material to allow accurate reading with minimal signal loss.

Accordingly, in a first exemplary embodiment, a downhole tractor 28 is positioned along coiled tubing 30 to which optical computing devices 22 are secured. When formation evaluation is desired, arms 32 of downhole tractor 28 are extended such that optical computing devices are in contact with, or in sufficient proximity to, the surface of formation 14. The required distance between the optical computing device and sample will be dictated, in part, by the strength of the electromagnetic radiation source utilized. Alternatively, other adjustable linkages may be utilized for this purpose, such as, for example, adjustable stabilizers or casing scrapers. The use of such linkages is well-known in the art.

In an alternate second exemplary embodiment, the housing of optical computing devices may be designed to allow material to flow past the optical components, as described herein, thus negating the need for adjustable linkages. Such designs may be especially useful in coring drilling applications, as the cuttings may be evaluated as they pass optical computing devices 22, thus indicating in real-time when a desired formation has been encountered.

Figure 6:
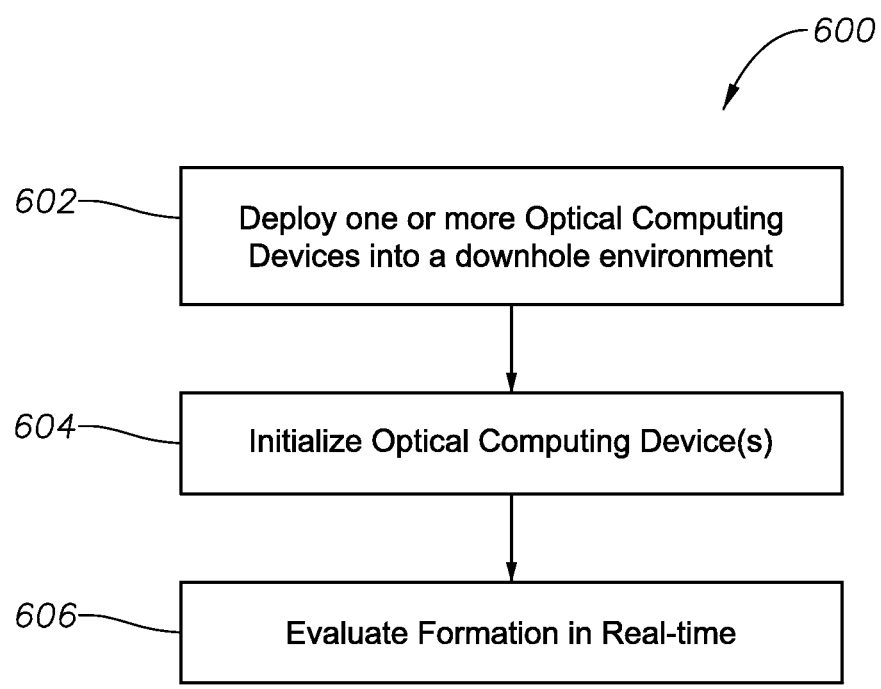
FIG. 6 is a flow chart of a formation evaluation methodology performed by an optical computing device in accordance to certain exemplary methods of the present invention.

FIG. 6 is a flow chart 600 of a formation evaluation methodology performed by an optical computing device in accordance to certain exemplary methods of the present invention. At block 602, one or more optical computing devices are deployed into a downhole environment. Such deployment may be by way of, for example, an evaluation tool positioned along a wireline or coiled tubing, which would allow multiple measurements as the evaluation tool is lowered into the wellbore. Alternatively, one or more optical computing devices may be permanently positioned at various positions along a workstring or casing tubulars. When it is desired to perform formation evaluation, CPU station 24 initializes one or more optical computing devices at block 604. In those embodiments utilizing adjustable linkages, the optical computing devices are positioned adjacent a formation of interest and the linkage is extended such that the optical computing devices are in close proximity to, or contacting the surface of, the formation. Then at block 606, the optical elements contained therein optically interact with the radiation emanating from the formation surface which, as described previously, is utilized to evaluate the formation in real-time.

Alternatively, in those embodiments utilizing a housing which allows fluid and/or material to flow therethrough, the optical elements interact with the sample fluid/material as it flows past the activated computing device to thereby evaluate the formation in real-time. The optical computing device (or the CPU station) may also utilize the radiation emanating from the sample to determine one or more other characteristics of the sample (presence of C1-C4 hydrocarbon, for example). The determination of block 606 may be performed in real-time by the optical computing device itself or formation characteristic data is generated by the computing device and transmitted to the CPU station for further processing in real-time.

Accordingly, the present invention provides an optical computing device that determines/monitors corrosion or evaluates formation data in real-time by deriving the data directly from the output of an optical element. The detected corrosion data may correspond to corrosive elements present in wellbore fluids, corrosive elements present on the surface of various downhole tools, etc. The detected formation data corresponds to formation chemistry, sand fraction, porosity, watercut, natural or man-made tags or tracers, for example, and may be evaluated against pre-defined formation evaluation parameters to determine whether a desired formation has been encountered.

The present invention provides a number of advantages. The ability to measure physical and environmental changes in real-time, independent of the optical computing device's primary function provides great advantage because, in addition to characteristic data, corrosive and formation data can be collected and transmitted with the original signal without the need for additional equipment, such as gauges or transducers. Additional savings can be realized because of the elimination of special handling procedures, protective equipment and transportation associated with conventional nuclear-type methods. Also, encountering a desired payzone may be achieved without the necessity of costly post-lab analysis of coring samples. Moreover, more elaborate mapping of the formation can be achieved through use of a plurality of downhole optical computing devices. Accordingly, the present invention provides the ability to monitor corrosion and evaluate formation data in real-time using a low-cost and highly compact device.

An exemplary methodology of the present invention provides a method utilizing an optical computing device to determine corrosion of a sample, the method comprising deploying an optical computing device into an environment, the optical computing device comprising an optical element and a detector; optically interacting electromagnetic radiation with a sample to produce sample-interacted light; optically interacting the optical element with the sample-interacted light to generate optically-interacted light which corresponds to a characteristic of the sample; generating a signal that corresponds to the optically-interacted light through utilization of the detector; and determining a corrosion of the sample using the signal. In another, the optical element is an Integrated Computational Element. In yet another, determining the corrosion of the sample further comprises comparing the signal to baseline data of the sample. In another, determining the corrosion of the sample further comprises determining the baseline data of the sample using the optical computing device at a time T1; and comparing the signal to the baseline data of the sample at a time T2.

In yet another, the baseline data of the sample is generated using empirical data. In another, the corrosion of the sample is determined in real-time. Another method further comprises utilizing the signal to generate a historical record of a rate of corrosion of the sample over time. Yet another method further comprises utilizing the signal to predict life expectancy of the sample. In another, determining the corrosion of the sample is achieved using a signal processor communicably coupled to the detector. In yet another, deploying the optical computing device further comprises deploying the optical computing device as at least one of part of a downhole tool extending along a wellbore; part of a casing extending along the wellbore; or part of a workstring extending along the wellbore. In another, the method further comprises utilizing the signal to determine whether remedial action is necessary.

An exemplary embodiment of the present invention provides an optical computing device to determine corrosion of a sample, comprising electromagnetic radiation that optically interacts with a sample to produce sample-interacted light; a first optical element that optically interacts with the sample-interacted light to produce optically-interacted light which corresponds to a characteristic of the sample; and a detector positioned to measure the optically-interacted light and thereby generate a signal utilized to determine corrosion of the sample. Another embodiment further comprises an electromagnetic radiation source that generates the electromagnetic radiation. Yet another embodiment further comprises a signal processor communicably coupled to the detector to computationally determine the corrosion of the sample in real-time. In another, the optical element is an Integrated Computational Element.

In yet another, the characteristic of the sample is at least one of an elemental corrosion by-product, material loss or physical defect of the sample. In another, the optical computing device comprises at least one of part of a downhole tool extending along a wellbore; part of a casing extending along the wellbore; or part of a workstring extending along the wellbore.

Another exemplary methodology of the present invention provides a method utilizing an optical computing device to determine corrosion of a sample, the method comprising deploying an optical computing device into an environment; and determining corrosion of the sample present within the environment using the optical computing device. In another, the environment is a wellbore and the corrosion is determined in real-time. In yet another, the optical element is an Integrated Computational Element.

Yet another exemplary methodology of the present invention provides a method utilizing an optical computing device to evaluate a downhole formation, the method comprising deploying an optical computing device into a downhole environment, the optical computing device comprising an optical element and a detector; optically interacting electromagnetic radiation with a formation sample to produce sample-interacted light; optically interacting the optical element with the sample-interacted light to generate optically-interacted light which corresponds to a characteristic of the formation sample; generating a signal that corresponds to the optically-interacted light through utilization of the detector; and evaluating the formation sample using the using the signal. In another, the optical element is an Integrated Computational Element. In yet another, deploying the optical computing device further comprises positioning the optical computing device adjacent to a surface of the formation along an open hole section of the downhole environment.

Another method further comprises utilizing an adjustable linkage to extend the optical computing device into proximity with the surface of the formation. In another, the characteristic of the sample comprises at least one of a formation chemistry data, sand fraction data, porosity data, watercut data, tracer data or tag data. In yet another, the formation is evaluated in real-time. In yet another, the formation is evaluated using a signal processor communicably coupled to the detector. In another, deploying the optical computing device further comprises deploying the optical computing device as at least one of part of a downhole tool extending along a wellbore; part of a casing extending along the wellbore; or part of a workstring extending along the wellbore.

Another exemplary embodiment of the present invention provides an optical computing device to evaluate a downhole formation, comprising electromagnetic radiation that optically interacts with a formation sample to produce sample-interacted light; a first optical element that optically interacts with the sample-interacted light to produce optically-interacted light which corresponds to a characteristic of the formation sample; and a detector positioned to measure the optically-interacted light and thereby generate a signal utilized to determine evaluate the formation sample. In another, the computing device further comprises an electromagnetic radiation source that generates the electromagnetic radiation. Yet another further comprises a signal processor communicably coupled to the detector to computationally evaluate the formation sample. In another, the optical element is an Integrated Computational Element. In yet another, the optical computing device is secured to an adjustable linkage positioned along a workstring, the adjustable linkage having an arm adapted to extend the optical computing device into proximity with a surface of the formation.

In another, the characteristic of the sample comprises at least one of a formation chemistry data, sand fraction data, porosity data, watercut data, tracer data or tag data. In yet another, the computing device further comprises a signal processor communicably coupled to the detector to evaluate the formation in real-time. In yet another, the optical computing device forms part of a downhole tool extending along a wellbore; a casing extending along the wellbore; or a workstring extending along the wellbore.

Another exemplary methodology of the present invention provides a method utilizing an optical computing device to evaluate a downhole formation, the method comprising deploying an optical computing device into a downhole environment; and evaluating a formation sample present within the environment using the optical computing device.

In another, the formation is evaluated in real-time. In yet another, the optical element is an Integrated Computational Element.

Although various embodiments and methodologies have been shown and described, the invention is not limited to such embodiments and methodologies, and will be understood to include all modifications and variations as would be apparent to one ordinarily skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:

1. A method utilizing an optical computing device to determine corrosion of a sample, the method comprising:
    deploying an optical computing device into an environment, the optical computing device comprising an optical element and a detector;
    optically interacting electromagnetic radiation with a sample to produce sample-interacted light;
    optically interacting the optical element with the sample-interacted light to generate optically-interacted light which corresponds to a characteristic of the sample;
    determining, at a time T1, baseline data of the sample using the optical computing device;
    generating a signal that corresponds to the optically-interacted light through utilization of the detector; and
    determining corrosion of the sample using the signal by comparing, at a time T2, the signal to the baseline data of the sample at a time T2 to thereby determine a spectral change between the signal and baseline data.

2. A method as defined in claim 1, wherein the optical element is an Integrated Computational Element.

3. A method as defined in claim 1, wherein the sample is a multiphase wellbore fluid.

4. A method as defined in claim 1, wherein the sample is selected from of a downhole tool component, a tubular, a rock formation, or a slurry.

5. A method as defined in claim 1, wherein the corrosion of the sample is determined in real-time.

6. A method as defined in claim 1, further comprising utilizing the signal to generate a historical record of a rate of corrosion of the sample over time.

7. A method as defined in claim 1, further comprising utilizing the signal to predict life expectancy of the sample.

8. A method as defined in claim 1, wherein determining the corrosion of the sample is achieved using a signal processor communicably coupled to the detector.

9. A method as defined in claim 1, wherein deploying the optical computing device further comprises deploying the optical computing device as at least one of:
    part of a downhole tool extending along a wellbore;
    part of a casing extending along the wellbore; or
    part of a workstring extending along the wellbore.

10. A method as defined in claim 1, further comprising utilizing the signal to determine whether remedial action is necessary.

11. An optical computing device to determine corrosion of a sample, comprising:
    electromagnetic radiation that optically interacts with a sample to produce sample-interacted light;
    a first optical element that optically interacts with the sample-interacted light to produce optically-interacted light which corresponds to a characteristic of the sample; and
    a detector positioned to measure the optically-interacted light and thereby generate a signal utilized to determine corrosion of the sample by comparing baseline spectral data of the sample corresponding to a time T1 to spectral data in the signal corresponding to a time T2 to thereby determine a spectral change between the signal and baseline data.

12. An optical computing device as defined in claim 11, further comprising an electromagnetic radiation source that generates the electromagnetic radiation.

13. An optical computing device as defined in claim 11, further comprising a signal processor communicably coupled to the detector to computationally determine the corrosion of the sample in real-time.

14. An optical computing device as defined in claim 11, wherein the optical element is an Integrated Computational Element.

15. An optical computing device as defined in claim 11, wherein the characteristic of the sample is at least one of an elemental corrosion by-product, material loss or physical defect of the sample.

16. An optical computing device as defined in claim 11, wherein the optical computing device comprises at least one of:
    part of a downhole tool extending along a wellbore;
    part of a casing extending along the wellbore; or
    part of a workstring extending along the wellbore.

17. A method utilizing an optical computing device to determine corrosion of a sample, the method comprising:
    deploying an optical computing device into an environment;
    obtaining baseline data of a sample within the environment at a time T1;
    obtaining a signal that corresponds to a characteristic of the sample at a time T2; and
    computing a shift in spectral information between the baseline data and signal to thereby determine corrosion of the sample using the optical computing device.

18. A method as defined in claim 17, wherein the environment is a wellbore and the corrosion is determined in real-time.

19. A method as defined in claim 17, wherein the optical computing device comprises an Integrated Computational Element.

20. A method utilizing an optical computing device to evaluate a downhole formation, the method comprising:
    deploying an optical computing device into a downhole environment as part of a downhole tool, the optical computing device comprising an optical element and a detector;
    using an adjustable linkage having an arm to extend the optical computing device from the downhole tool and into proximity with a surface of the formation;
    optically interacting electromagnetic radiation with a formation sample to produce sample-interacted light;
    optically interacting the optical element with the sample-interacted light to generate optically-interacted light which corresponds to a characteristic of the formation sample;
    generating a signal that corresponds to the optically-interacted light through utilization of the detector; and
    evaluating the formation sample.

21. A method as defined in claim 20, wherein the optical element is an Integrated Computational Element.

22. A method as defined in claim 20, wherein deploying the optical computing device further comprises positioning the optical computing device adjacent to a surface of the formation along an open hole section of the downhole environment.

23. A method as defined in claim 20, wherein the characteristic of the formation sample comprises at least one of a formation chemistry data, sand fraction data, porosity data, watercut data, tracer data or tag data.

24. A method as defined in claim 20, wherein the formation is evaluated in real-time.

25. A method as defined in claim 20, wherein the formation is evaluated using a signal processor communicably coupled to the detector.

26. A method as defined in claim 20, wherein deploying the optical computing device further comprises deploying the optical computing device as at least one of:
   part of a downhole tool extending along a wellbore;
   part of a casing extending along the wellbore; or
   part of a workstring extending along the wellbore.

27. An optical computing device to evaluate a downhole formation, comprising:
   electromagnetic radiation that optically interacts with a formation sample to produce sample-interacted light;
   an optical element that optically interacts with the sample-interacted light to produce optically-interacted light which corresponds to a characteristic of the formation sample; and
   a detector positioned to measure the optically-interacted light and thereby generate a signal utilized to evaluate the formation sample,
   wherein the optical computing device is secured to an adjustable linkage positioned along a workstring, the adjustable linkage having an arm adapted to extend the optical computing device from the workstring and into proximity with a surface of the formation.

28. An optical computing device as defined in claim 27, further comprising an electromagnetic radiation source that generates the electromagnetic radiation.

29. An optical computing device as defined in claim 27, wherein the optical element is an Integrated Computational Element.

30. An optical computing device as defined in claim 27, wherein the characteristic of the formation sample comprises at least one of a formation chemistry data, sand fraction data, porosity data, watercut data, tracer data or tag data.

31. An optical computing device as defined in claim 27, further comprising a signal processor communicably coupled to the detector to evaluate the formation in real-time.

32. An optical computing device as defined in claim 27, wherein the optical computing device forms part of:
   a downhole tool extending along a wellbore;
   a casing extending along the wellbore; or
   a workstring extending along the wellbore.

33. A method utilizing an optical computing device to evaluate a downhole formation, the method comprising:
   deploying an optical computing device into a downhole environment;
   evaluating a first sample present within the environment using the optical computing device, the first sample being a formation sample;
   evaluating a second sample present within the environment using the optical computing device; and
   determining corrosion of the second sample by comparing the second sample to baseline data of the second sample to thereby determine a spectral change between the second sample and baseline data.

34. A method as defined in claim 33, wherein the first and second samples are evaluated in real-time.

35. A method as defined in claim 33, wherein the optical computing device comprises an Integrated Computational Element.

* * * * *